United States Patent
Dibas et al.

(10) Patent No.: US 9,283,217 B2
(45) Date of Patent: *Mar. 15, 2016

(54) PHARMACEUTICAL COMPOSITIONS COMPRISING 7-(1 H-IMIDAZOL-4-YLMETHYL)-5,6,7,8-TETRAHYDRO-QUINOLINE FOR TREATING SKIN DISEASES AND CONDITIONS

(71) Applicant: Allergan, Inc., Irvine, CA (US)

(72) Inventors: Mohammed I. Dibas, Laguna Niguel, CA (US); Edward C. Hsia, Irvine, CA (US); John E. Donello, Dana Point, CA (US); Daniel W. Gil, Corona Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/830,311

(22) Filed: Mar. 14, 2013

(65) Prior Publication Data

US 2013/0203809 A1    Aug. 8, 2013

Related U.S. Application Data

(63) Continuation-in-part of application No. 13/672,475, filed on Nov. 8, 2012.

(60) Provisional application No. 61/558,104, filed on Nov. 10, 2011.

(51) Int. Cl.
*A61K 31/4709* (2006.01)

(52) U.S. Cl.
CPC .................................. *A61K 31/4709* (2013.01)

(58) Field of Classification Search
CPC .................................................. A61K 31/4709
See application file for complete search history.

(56) References Cited

U.S. PATENT DOCUMENTS

| | | | |
|---|---|---|---|
| 6,387,383 B1 | 5/2002 | Dow | |
| 6,468,989 B1 | 10/2002 | Chang | |
| 6,517,847 B2 | 2/2003 | Dow | |
| 6,680,062 B2 | 1/2004 | Muizzuddin | |
| 7,323,477 B2 | 1/2008 | Chow | |
| 7,439,241 B2 | 10/2008 | DeJovin | |
| 7,491,383 B2 | 2/2009 | Woodward | |
| 7,812,049 B2 | 10/2010 | Shanler | |
| 7,943,641 B2 | 5/2011 | Chow | |
| 2005/0020600 A1 | 1/2005 | Scherer | |
| 2011/0118267 A1 | 5/2011 | DeJovin | |
| 2012/0035123 A1 | 2/2012 | Jomard | |

FOREIGN PATENT DOCUMENTS

WO    2009-052073    4/2009

OTHER PUBLICATIONS

Baldwin, Hilary, Diagnosis and Treatment of Rosacea: State of the Art, Journal of Drugs in Dermatology, Jun. 2012, 725-730, 11(6).
Gennaro, Alfonso, Remington: The Science and Practice of Pharmacy, 1995, 1517-1518, 2.
Gennaro, Alfonso, Remington: The Science and Practice of Pharmacy, 1995, 282-291, 1.
Gotoh, Yoshikazu et al, Clonidine Inhibits Itch-Related Response Through Stimulation of α2-Adrenoceptors in the Spinal Cord in Mice, European Journal of Pharmacology, Jan. 10, 2011, 215-219, 650 (1).
Stahl, Heinrich et al, Handbook of Pharmaceutical Salts, Verlag Helvetica Chimica Acta—Zurich, 2002, 329-345.
Tulandi, Togas et al, Effect of Guanfacine, An Alpha-Adrenergic Agonist, on Menopausal Flushing, Maturitas, 1986, 197-200, 8 (3).
Patent Cooperation Treaty, Notification of Transmittal of the International Search Report and the Written Opinion of the International Searching Authority, or the Declaration, Form PCT/ISA/220, Int. App. No. PCT/US2012/064075, Jan. 1, 2013.

*Primary Examiner* — Sreeni Padmanabhan
*Assistant Examiner* — Jody Karol
(74) *Attorney, Agent, or Firm* — Barbara C. Potts

(57) ABSTRACT

The present invention relates to a method for treating skin diseases and skin conditions in a patient in need thereof which comprises of administering a therapeutically effective amount of a pharmaceutical composition comprising a therapeutically effective amount of 7-(1H-Imidazol-4-ylmethyl)-5,6,7,8-tetrahydro-quinoline, or its individual enantiomers or the tautomers thereof, or a pharmaceutically acceptable salt thereof.

4 Claims, 7 Drawing Sheets

Group A = Vehicle
Group B = (S)-(+)-7-(1H-Imidazol-4-ylmethyl)-5,6,7,8-tetrahydro-quinoline
# p< 0.05, ## p<0.01 vs Exposed Control
* p< 0.05, ** p<0.01 vs Group A

PHARMACEUTICAL COMPOSITIONS COMPRISING 7-(1 H-IMIDAZOL-4-YLMETHYL)-5,6,7,8-TETRAHYDRO-QUINOLINE FOR TREATING SKIN DISEASES AND CONDITIONS

RELATED APPLICATION

This application is a continuation-in-part of U.S. patent application Ser. No. 13/672,475, filed Nov. 8, 2012, which claims the benefit of U.S. Provisional Application Ser. No. 61/558,104, filed Nov. 10, 2011, the disclosure of which are hereby incorporated in their entirety herein by reference.

BACKGROUND OF THE INVENTION

The present invention relates to a method for treating skin diseases and skin conditions in a patient in need thereof which comprises administering a pharmaceutical composition comprising a therapeutically effective amount of 7-(1H-imidazol-4-ylmethyl)-5,6,7,8-tetrahydro-quinoline or the enantiomers thereof, or the tautomers thereof, or pharmaceutically acceptable salts thereof.

SUMMARY OF THE RELATED ART

Three alpha 1 and three alpha 2 adrenergic receptors have been characterized by molecular and pharmacological methods. Activation of these alpha receptors evokes physiological responses having useful therapeutic actions. Alpha adrenergic agonists act on the peripheral vasculature to cause vasoconstriction and thereby ameliorate the symptoms of inflammatory skin disorders, including erythema or redness. Alpha adrenergic agonists are useful for ocular mucosal tissue to treat conjunctival redness (hyperemia), for nasal mucosa, as a decongestant for the treatment of allergic rhinitis, and for rectal mucosal administration suitable for treating and curing hemorrhoids.

H. E. Baldwin describes the diagnosis and the actual treatments of rosacea and related skin diseases, in the Journal of Drugs in Dermatology 2012, Vol. 11(6) pages 725-730.

U.S. Pat. No. 6,680,062 discloses topical cosmetic and pharmaceutical compositions for the treatment of the skin.

U.S. Patent Application Publication No. 2012/0035123 describes combinations of compounds for treating skin diseases.

U.S. Pat. No. 7,812,049 discloses a method for treating erythema resulting from rosacea comprising oxymetazoline. Oxymetazoline is a selective alpha-1 agonist and partial alpha-2 agonist topical decongestant.

Compound 7-(1H-imidazol-4-ylmethyl)-5,6,7,8-tetrahydro-quinoline is known as a potent alpha 1 and alpha 2 adrenergic receptor pan agonist. The racemic mixture and the two enantiomers of 7-(1H-imidazol-4-ylmethyl)-5,6,7,8-tetrahydro-quinoline are disclosed in U.S. Pat. No. 7,323,477 B2. U.S. Pat. No. 7,943,641 discloses a composition comprising (S)-(+)-7-(1H-Imidazol-4-ylmethyl)-5,6,7,8-tetrahydroquinoline for the treatment of glaucoma or ocular hypertension.

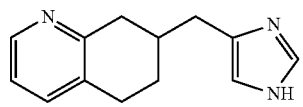
7-((1H-imidazol-4-yl)methyl)-5,6,7,8-tetrahydroquinoline

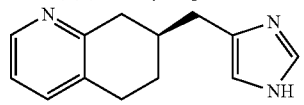
(R)-(−)-7-((1H-imidazol-4-yl)methyl)-5,6,7,8-tetrahydroquinoline

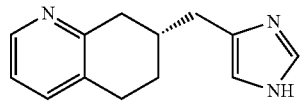
(S)-(+)-7-((1H-imidazol-4-yl)methyl)-5,6,7,8-tetrahydroquinoline

BRIEF SUMMARY OF THE INVENTION

It has now been discovered that the pharmaceutical compositions of (S)-(+)-7-(1H-Imidazol-4-ylmethyl)-5,6,7,8-tetrahydro-quinoline are useful for the treatment of skin diseases and skin conditions.

The present invention relates to pharmaceutical compositions containing as active ingredient 7-(1H-Imidazol-4-ylmethyl)-5,6,7,8-tetrahydro-quinoline for treatment of skin diseases and skin conditions.

In another aspect the present invention relates to pharmaceutical compositions containing as active ingredient (S)-(+)-7-(1H-Imidazol-4-ylmethyl)-5,6,7,8-tetrahydro-quinoline for treatment of skin diseases and skin conditions.

In another aspect the present invention relates to pharmaceutical compositions containing as active ingredient (R)-(−)-7-(1H-Imidazol-4-ylmethyl)-5,6,7,8-tetrahydro-quinoline for treatment of skin diseases and skin conditions.

In another aspect the present invention relates to a method for treating skin diseases in a patient in need thereof which comprises administering a pharmaceutical composition comprising a therapeutically effective amount of 7-(1H-Imidazol-4-ylmethyl)-5,6,7,8-tetrahydro-quinoline or a pharmaceutically acceptable salt thereof.

In another aspect the present invention relates to a method for treating skin diseases in a patient in need thereof which comprises administering a pharmaceutical composition comprising a therapeutically effective amount of (S)-(+)-7-(1H-Imidazol-4-ylmethyl)-5,6,7,8-tetrahydro-quinoline or a pharmaceutically acceptable salt thereof.

In another aspect the present invention relates to a method for treating skin diseases in a patient in need thereof which comprises administering a pharmaceutical composition comprising a therapeutically effective amount of (R)-(−)-7-(1H-Imidazol-4-ylmethyl)-5,6,7,8-tetrahydro-quinoline or a pharmaceutically acceptable salt thereof.

In another aspect the present invention relates to a method for improving skin diseases in a patient in need thereof which comprises administering a pharmaceutical composition comprising a therapeutically effective amount of 7-(1H-Imidazol-4-ylmethyl)-5,6,7,8-tetrahydro-quinoline or a pharmaceutically acceptable salt thereof.

In another aspect the present invention relates to a method for improving skin diseases in a patient in need thereof which comprises administering a pharmaceutical composition comprising a therapeutically effective amount of (S)-(+)-7-(1H-Imidazol-4-ylmethyl)-5,6,7,8-tetrahydro-quinoline or a pharmaceutically acceptable salt thereof.

In another aspect the present invention relates to a method for improving skin diseases in a patient in need thereof which comprises administering a pharmaceutical composition comprising a therapeutically effective amount of (R)-(−)-7-(1H-Imidazol-4-ylmethyl)-5,6,7,8-tetrahydro-quinoline or a pharmaceutically acceptable salt thereof.

The compound may be administered through different routes, including but not limited to, topical dermatological application of an effective dose, direct injection, or formulations that may further enhance the long duration of action such as slow releasing pellets, suspensions, gels, solutions, creams, ointments, foams, emulsions, microemulsions, milks, patches, serums, aerosols, sprays, dispersions, microcapsules, vesicles, microparticles, wet cloths, dry cloths, facial cloths, or sustained delivery devices such as any suitable drug delivery system known in the art.

DETAILED DESCRIPTION OF THE INVENTION

Figure 1:
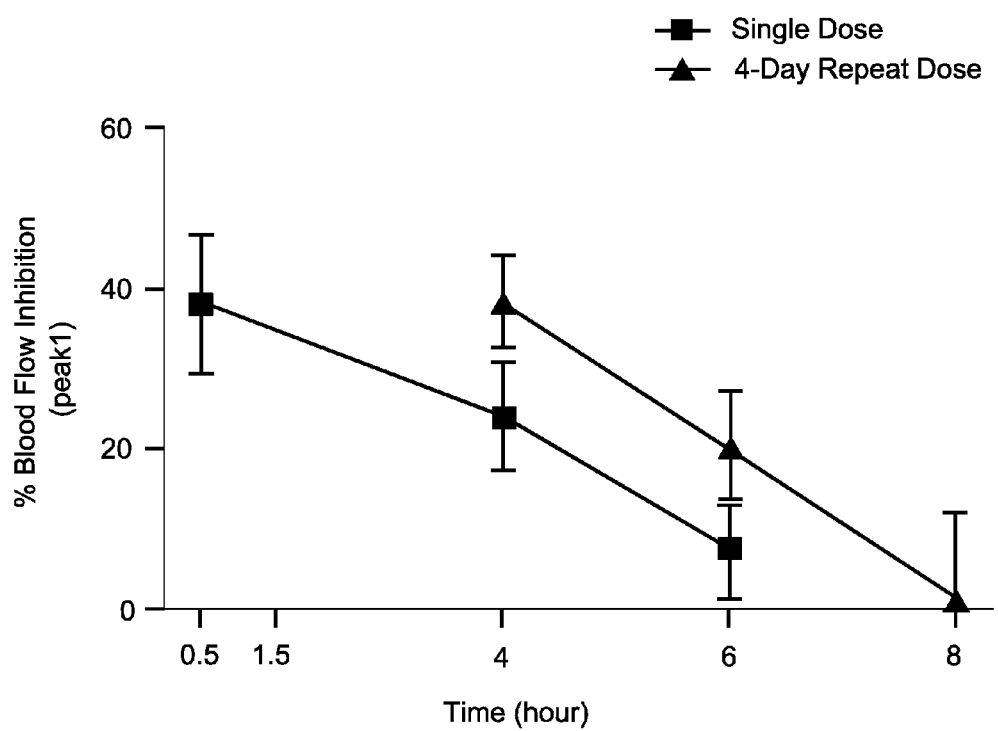
FIG. 1 shows topical (S)-(+)-7-(1H-Imidazol-4-ylmethyl)-5,6,7,8-tetrahydro-quinoline inhibits 37° C.-induced cutaneous vessel dilation in rat paws for at least 4 hrs post-treatment following a single application and for at least 6 hrs post-treatment following 4 daily applications.

In one aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of 7-(1H-Imidazol-4-ylmethyl)-5,6,7,8-tetrahydro-quinoline, or the enantiomers thereof, or the tautomers thereof, or pharmaceutically acceptable salts thereof.

In another aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of (S)-(+)-7-(1H-Imidazol-4-ylmethyl)-5,6,7,8-tetrahydro-quinoline, or the tautomers thereof, or pharmaceutically acceptable salts thereof.

In another aspect of the invention, there is provided a method for treating skin diseases and skin conditions in a patient in need thereof which comprises, consists essentially of or consists of administering a therapeutically effective amount of a pharmaceutical composition comprising, consisting essentially of or consisting of a therapeutically effective amount of (R)-(−)-7-(1H-Imidazol-4-ylmethyl)-5,6,7,8-tetrahydro-quinoline, or the tautomers thereof, or pharmaceutically acceptable salts thereof.

By "skin diseases" it should be understood any condition, complaint or affliction associated with the listed diseases.

Skin diseases and skin conditions which may be treated with pharmaceutical compositions containing as active ingredient 7-(1H-Imidazol-4-ylmethyl)-5,6,7,8-tetrahydro-quinoline or its enantiomers either: (S)-(+)-7-(1H-Imidazol-4-ylmethyl)-5,6,7,8-tetrahydro-quinoline or (R)-(−)-7-(1H-Imidazol-4-ylmethyl)-5,6,7,8-tetrahydro-quinoline include, but are not limited to: rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritus, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema.

Skin conditions which result in rosacea can be induced by intake of spicy food, of alcohol, of chocolate, of hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics or psychological stress.

The actual amount of the compound to be administered in any given case will be determined by a physician taking into account the relevant circumstances, such as the severity of the condition, the age and weight of the patient, the patient's general physical condition, the cause of the condition, and the route of administration.

In another aspect of the invention, there is provided a method for treating skin diseases wherein the pharmaceutical composition comprising, consisting essentially of or consisting of a therapeutically effective amount of 4-bromo-N-(imidazolidin-2-ylidene)-1H-benzimidazol-5-amine, is selected from topical skin application comprising suspensions, gels, solutions, creams, lotions, ointments, foams, emulsions, microemulsions, milks, serums, aerosols, sprays, dispersions, microcapsules, vesicles, microparticles, wet cloths, dry cloths, facial cloths, applications and formulations that may further enhance the long duration of actions such as a slow releasing pellets, direct injection, or sustained delivery devices such as any suitable drug delivery systems known in the art. Pharmaceutical compositions of the present invention can be used for the topical administration including solutions, gels, lotions creams, ointments, foams, mousses, emulsions, microemulsions, milks, serums, aerosols, sprays, dispersions, patches, micelles, liposomes, microcapsules, vesicles and microparticles thereof.

Emulsions, such as creams and lotions that can be used as topical carriers and their preparation are disclosed in Remington: The Science and Practice of Pharmacy 282-291 (Alfonso R. Gennaro Ed. 19$^{th}$ ed. 1995) hereby incorporated herein by reference.

Suitable gels for use in the invention are disclosed in Remington: The Science and Practice of Pharmacy 1517-1518 (Alfonso R. Gennaro Ed. 19$^{th}$ ed. 1995) hereby incorporated herein by reference. Other suitable gels for use within the invention are disclosed in U.S. Pat. No. 6,387,383, U.S. Pat. No. 6,517,847 and U.S. Pat. No. 6,468,989.

In another aspect of the invention, there is provided a method for improving skin diseases, by administering to a patient in need thereof a pharmaceutical composition containing as active ingredient 7-(1H-Imidazol-4-ylmethyl)-5,6,7,8-tetrahydro-quinoline, including but not limited to: rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritus, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema.

In another aspect of the invention, there is provided a method for improving skin diseases, by administering to a patient in need thereof a pharmaceutical composition containing as active ingredient (S)-(+)-7-(1H-Imidazol-4-ylmethyl)-5,6,7,8-tetrahydro-quinoline, including but not limited to: rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritus, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema.

In another aspect of the invention, there is provided a method for improving skin diseases, by administering to a patient in need thereof a pharmaceutical composition containing as active ingredient (R)-(−)-7-(1H-Imidazol-4-ylmethyl)-5,6,7,8-tetrahydro-quinoline, including but not limited to: rosacea, rosacea fulminans, sunburn, psoriasis, menopause-associated hot flashes, flushing and redness associated with hot flashes, erythema associated with hot flashes, hot flashes resulting from orchiectomyatopic dermatitis, treatment of redness and itch from insect bites, photoaging, seborrheic dermatitis, acne, allergic dermatitis, telangiectasia (dilations of previously existing small blood vessels) of the face, angioectasias, rhinophyma (hypertrophy of the nose with follicular dilation), acne-like skin eruptions (may ooze or crust), burning or stinging sensation, erythema of the skin, cutaneous hyperactivity with dilation of blood vessels of the skin, Lyell's syndrome, Stevens-Johnson syndrome, local itching and discomfort associated with hemorrhoids, hemorrhoids, erythema multiforme minor, erythema multiforme major, erythema nodosum, eye puffiness, urticaria, pruritus, purpura, varicose veins, contact dermatitis, atopic dermatitis, nummular dermatitis, generalized exfoliative dermatitis, stasis dermatitis, lichen simplex chronicus, perioral dermatitis, pseudofolliculitis barbae, granuloma annulare, actinic keratosis, basal cell carcinoma, squamous cell carcinoma, eczema.

In another aspect of the invention, there is provided a method of decreasing the irritation of skin associated with rosacea treatment regimen of topically applied a therapeutically effective amount of 7-(1H-Imidazol-4-ylmethyl)-5,6,7,8-tetrahydro-quinoline, the method of treating telangiectasia or angioectasias with a therapeutically effective amount of 7-(1H-Imidazol-4-ylmethyl)-5,6,7,8-tetrahydro-quinoline, and therefore, it also includes the method of reducing redness associated with the appearance of rosacea.

In another aspect of the invention, there is provided a method of decreasing the irritation of skin associated with rosacea treatment regimen of topically applied a therapeutically effective amount of (S)-(+)-7-(1H-Imidazol-4-ylmethyl)-5,6,7,8-tetrahydro-quinoline, the method of treating telangiectasia or angioectasias with a therapeutically effective amount of (S)-(+)-7-(1H-Imidazol-4-ylmethyl)-5,6,7,8-tetrahydro-quinoline, and therefore, it also includes the method of reducing redness associated with the appearance of rosacea.

In another aspect of the invention, there is provided a method of decreasing the irritation of skin associated with rosacea treatment regimen of topically applied a therapeutically effective amount of (R)-(−)-7-(1H-Imidazol-4-ylmethyl)-5,6,7,8-tetrahydro-quinoline, the method of treating telangiectasia or angioectasias with a therapeutically effective amount of (R)-(−)-7-(1H-Imidazol-4-ylmethyl)-5,6,7,8-tetrahydro-quinoline, and therefore, it also includes the method of reducing redness associated with the appearance of rosacea.

In another aspect of the invention, there is provided a method for treating skin diseases including but not limited to: rosacea induced by intake of spicy food, chocolate, alcohol, hot or alcoholic drinks, temperature variations, heat, exposure to ultraviolet or infrared radiation, exposure to low relative humidity, exposure of the skin to strong winds or currents of air, exposure of the skin to surfactants, irritants, irritant dermatological topical agents, and cosmetics or psychological stress. (S)-(+)-7-(1H-Imidazol-4-ylmethyl)-5,6,7,8-tetrahydro-quinoline may be formulated with efficacy enhancing components as disclosed in U.S. Pat. No. 7,491,383 B2.

In another aspect of the invention, there is provided an article of manufacture comprising packaging material and a pharmaceutical agent contained within said packaging material, wherein the pharmaceutical agent is therapeutically effective for treating a skin disease and wherein the packaging material comprises a label which indicates the pharmaceutical agent can be used for treating a skin disease and wherein said pharmaceutical agent comprises an effective amount of 7-(1H-Imidazol-4-ylmethyl)-5,6,7,8-tetrahydro-quinoline or a salt thereof.

In another aspect of the invention, there is provided an article of manufacture comprising packaging material and a pharmaceutical agent contained within said packaging material, wherein the pharmaceutical agent is therapeutically effective for treating a skin disease and wherein the packaging material comprises a label which indicates the pharmaceutical agent can be used for treating a skin disease and wherein said pharmaceutical agent comprises an effective amount of (S)-(+)-7-(1H-Imidazol-4-ylmethyl)-5,6,7,8-tetrahydro-quinoline or a salt thereof.

In another aspect of the invention, there is provided an article of manufacture comprising packaging material and a pharmaceutical agent contained within said packaging material, wherein the pharmaceutical agent is therapeutically effective for treating a skin disease and wherein the packaging material comprises a label which indicates the pharmaceutical agent can be used for treating a skin disease and wherein said pharmaceutical agent comprises an effective amount of (R)-(−)-7-(1H-Imidazol-4-ylmethyl)-5,6,7,8-tetrahydro-quinoline or a salt thereof.

In another aspect of the invention, there is provided a method for treating ocular diseases and conditions in a patient in need thereof which comprises, consists essentially of or consists of administering a therapeutically effective amount of a pharmaceutical composition comprising, consisting essentially of or consisting of a therapeutically effective amount of 7-(1H-Imidazol-4-ylmethyl)-5,6,7,8-tetrahydro-quinoline, or the enantiomers thereof, or the tautomers thereof, or pharmaceutically acceptable salts thereof.

In another aspect of the invention, there is provided a method for treating ocular diseases and conditions in a patient in need thereof which comprises, consists essentially of or consists of administering a therapeutically effective amount of a pharmaceutical composition comprising, consisting essentially of or consisting of a therapeutically effective amount of (S)-(+)-7-(1H-Imidazol-4-ylmethyl)-5,6,7,8-tetrahydro-quinoline, or the tautomers thereof, or pharmaceutically acceptable salts thereof.

In another aspect of the invention, there is provided a method for treating ocular diseases and conditions in a patient in need thereof which comprises, consists essentially of or consists of administering a therapeutically effective amount of a pharmaceutical composition comprising, consisting essentially of or consisting of a therapeutically effective amount of (R)-(−)-7-(1H-Imidazol-4-ylmethyl)-5,6,7,8-tetrahydro-quinoline, or the tautomers thereof, or pharmaceutically acceptable salts thereof.

By "ocular diseases" it should be understood any condition, complaint or affliction associated with the listed diseases.

Ocular diseases and conditions which may be treated with pharmaceutical compositions containing as active ingredient 7-(1H-Imidazol-4-ylmethyl)-5,6,7,8-tetrahydro-quinoline or its enantiomers either: (S)-(+)-7-(1H-Imidazol-4-ylmethyl)-5,6,7,8-tetrahydro-quinoline or (R)-(−)-7-(1H-Imidazol-4-ylmethyl)-5,6,7,8-tetrahydro-quinoline include, but are not limited to: ocular rosacea, pterygium, redness, hyperemia, conjunctival hyperemia, corneal neovascularization, ocular cicatricial pemphigoid and Stevens-Johnson syndrome.

The (S)-(+)-7-(1H-Imidazol-4-ylmethyl)-5,6,7,8-tetrahydro-quinoline compound has physiochemical and pharmacokinetic properties that are beneficial for sustained activity, particularly when the drug is delivered continuously (e.g. to the skin by a dermal patch).

"Pharmaceutical composition," as used here, means a composition that is suitable for administering to human patients for disease treatment. In one embodiment the compound of the invention is formulated as a pharmaceutically acceptable salt which further includes one or more organic or inorganic carriers or excipients suitable for dermatological applications. The pharmaceutically acceptable excipients may include one or more skin-penetrating agents, moisturizers, preservatives, gelling agents, protective agents, oil-in-water, water-in-oil, water-in-oil-in-water, and oil-in-water-in-silicon emulsions. The pharmaceutical composition may comprise excipients, binders, lubricants, solvents, disintegrants, or enhancers of cutaneous penetration and will be administered preferably topically. The active ingredient is used in an amount of about 0.01% up to about 20% and preferably about 0.1% to about 10% by weight based on the total weight of the composition.

"Pharmaceutically acceptable salt" refers to those salts which retain the biological effectiveness and properties of the free base and which are obtained by reaction with inorganic acids such as hydrochloric acid, hydrobromic acid, sulfuric acid, nitric acid, phosphoric acid, or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and, salicylic acid and the like (Handbook of Pharmaceutical Salts, P. Heinrich Stahl & Camille G. Wermuth (Eds), Verlag Helvetica Chimica Acta-Zürich, 2002, 329-345).

In another aspect of the invention, there is provided a method for treating skin diseases and skin conditions wherein the pharmaceutical composition comprising, consisting essentially of, or consisting of a therapeutically effective amount of 7-(1H-Imidazol-4-ylmethyl)-5,6,7,8-tetrahydro-quinoline is selected from topical skin application, direct injection, applications and formulations that may further enhance the long duration of actions such as a slow releasing pellet, suspension, gel, solution, cream, ointment, foams, emulsions, microemulsions, milks, serums, aerosols, sprays, dispersions, microcapsules, vesicles, microparticles, wet cloths, dry cloths, facial cloths.

In another aspect of the invention, there is provided a method for treating skin diseases and skin conditions wherein the pharmaceutical composition comprising, consisting essentially of, or consisting of a therapeutically effective amount of (R)-(−)-7-(1H-Imidazol-4-ylmethyl)-5,6,7,8-tetrahydro-quinoline is selected from topical skin application, direct injection, applications and formulations that may further enhance the long duration of actions such as a slow releasing pellet, suspension, gel, solution, cream, ointment, foams, emulsions, microemulsions, milks, serums, aerosols, sprays, dispersions, microcapsules, vesicles, microparticles, wet cloths, dry cloths, facial cloths.

In another aspect of the invention, there is provided a method for treating skin diseases and skin conditions wherein the pharmaceutical composition comprising, consisting essentially of, or consisting of a therapeutically effective amount of (S)-(+)-7-(1H-Imidazol-4-ylmethyl)-5,6,7,8-tetrahydro-quinoline is selected from topical skin application, direct injection, applications and formulations that may further enhance the long duration of actions such as a slow releasing pellet, suspension, gel, solution, lotion, cream, ointment, foams, emulsions, microemulsions, milks, serums, aerosols, sprays, dispersions, microcapsules, vesicles, microparticles, wet cloths, soaps, cleansing bars, dry cloths, facial cloths.

The present invention may be used in conjunction with rosacea treatments of topically applied agents such as macrocyclic lactones of the avermectin family, macrolides known as milbemycins, other alpha 1 or alpha 2 receptor agonists, retinoids, phytosphingosine, green tea extract, azelaic acid.

In another aspect, the present invention may be used to alleviate the pain or discomfort associated with aesthetic or plastic surgery or cosmetology procedures in combination with an anesthetic. Such procedures are, but not limited to, dermal filler injections, neurotoxin injections, Botulinum toxin injections, laser procedures, breast augmentations, breast lifts, breast reductions, face lifts, tummy tucks.

In another aspect, the present invention may be used as a local anti-inflammatory agent in combination with a steroid or a non-steroidal anti-inflammatory agent. Due to the vasoconstrictive properties of the compounds of the present invention, such combination can be applied topically at the site of inflammation or can be injected at the site of inflammation so that the composition is retained at the inflammation site for a sufficient period to treat various joint and muscle inflammatory conditions.

In another aspect, the present invention may be used to promote healing of various forms of tissue trauma, such as bruising, burns (including those caused by chemicals and heat) incisions, excisions, ulcers, such as diabetic ulcers and pressure ulcers. The present invention may also be used to improve the outcome of healing to prevent the formation of hypertrophic scars and keloids.

In another aspect, the present invention may be used for treating inflammatory conditions of joints or muscles at the site of inflammation, in a patient suffering thereof, which comprises treating said patient with a pharmaceutical composition comprising a therapeutically effective amount of 7-(1H-Imidazol-4-ylmethyl)-5,6,7,8-tetrahydro-quinoline or the individual enantiomers thereof, or the individual tautomers thereof, or a pharmaceutically acceptable salt thereof in combination with a steroid or a non-steroidal anti-inflammatory agent.

In another aspect, the present invention may be used for treating inflammatory conditions of joints or muscles at the site of inflammation, in a patient suffering thereof, which comprises treating said patient with a pharmaceutical composition comprising a therapeutically effective amount of (R)-(−)-7-(1H-Imidazol-4-ylmethyl)-5,6,7,8-tetrahydro-quinoline or the individual enantiomers thereof, or the individual tautomers thereof, or a pharmaceutically acceptable salt thereof in combination with a steroid or a non-steroidal anti-inflammatory agent.

In another aspect, the present invention may be used for treating inflammatory conditions of joints or muscles at the site of inflammation, in a patient suffering thereof, which comprises treating said patient with a pharmaceutical composition comprising a therapeutically effective amount of (S)-(+)-7-(1H-Imidazol-4-ylmethyl)-5,6,7,8-tetrahydro-quinoline or the individual enantiomers thereof, or the individual tautomers thereof, or a pharmaceutically acceptable salt thereof in combination with a steroid or a non-steroidal anti-inflammatory agent.

In another aspect, the present invention may be used for promoting healing of various forms of tissue trauma in a patient suffering thereof, which comprises treating said patient with a pharmaceutical composition comprising a therapeutically effective amount of 7-(1H-Imidazol-4-ylmethyl)-5,6,7,8-tetrahydro-quinoline, or the individual enantiomers thereof, or the individual tautomers thereof, or a pharmaceutically acceptable salt thereof.

In another aspect, the present invention may be used for promoting healing of various forms of tissue trauma in a patient suffering thereof, which comprises treating said patient with a pharmaceutical composition comprising a therapeutically effective amount of (R)-(−)-7-(1H-Imidazol-4-ylmethyl)-5,6,7,8-tetrahydro-quinoline, or the individual enantiomers thereof, or the individual tautomers thereof, or a pharmaceutically acceptable salt thereof.

In another aspect, the present invention may be used for promoting healing of various forms of tissue trauma in a patient suffering thereof, which comprises treating said patient with a pharmaceutical composition comprising a therapeutically effective amount of (S)-(+)-7-(1H-Imidazol-4-ylmethyl)-5,6,7,8-tetrahydro-quinoline, or the individual enantiomers thereof, or the individual tautomers thereof, or a pharmaceutically acceptable salt thereof.

In another aspect, the present invention may be used for alleviating the discomfort associated with aesthetic or plastic surgery or cosmetology procedures in a patient in need thereof, which comprises treating said patient with a pharmaceutical composition comprising a therapeutically effective amount of 7-(1H-Imidazol-4-ylmethyl)-5,6,7,8-tetrahydro-quinoline, or the individual enantiomers thereof, or the individual tautomers thereof, or a pharmaceutically acceptable salt thereof in combination with an anesthetic.

In another aspect, the present invention may be used for alleviating the discomfort associated with aesthetic or plastic surgery or cosmetology procedures in a patient in need thereof, which comprises treating said patient with a pharmaceutical composition comprising a therapeutically effective amount of (R)-(−)-7-(1H-Imidazol-4-ylmethyl)-5,6,7,8-tetrahydro-quinoline, or the individual enantiomers thereof, or the individual tautomers thereof, or a pharmaceutically acceptable salt thereof in combination with an anesthetic.

In another aspect, the present invention may be used for alleviating the discomfort associated with aesthetic or plastic surgery or cosmetology procedures in a patient in need thereof, which comprises treating said patient with a pharmaceutical composition comprising a therapeutically effective amount of (S)-(+)-7-(1H-Imidazol-4-ylmethyl)-5,6,7,8-tetrahydro-quinoline, or the individual enantiomers thereof, or the individual tautomers thereof, or a pharmaceutically acceptable salt thereof in combination with an anesthetic.

The present invention may also be used in conjunction with other classes of compounds such as:

Antimicrobials (such as antiparasitic, antibacterial, antifungal, antiviral);

Metronidazole, ivermectin, clindamycin, erythromycin, tetracycline, doxycycline, minocycline; Steroidal and non-steroidal anti-inflammatory agents (such as corticosteroids, tacrolimus, pimecrolimus, cyclosporine A);

Antiangiogenesis agents;

Antimycobacterial agents (such as dapsone);

Sunscreens or sunblocks or anything that functions like a sunscreen/sunblock (such as titanium dioxide, zinc oxide, avobenzone);

Antioxidants (such as Vitamins C, E, quercetin, resveratrol);

Other alpha agonists (such as brimonidine, oxymetazoline, clonidine);

Beta blockers (such as nadolol, propanolol, carvedilol);

Antihistamines;

Retinoids (such as tretinoin, adapalene, tazarotene, isotretinoin, retinaldehyde) Benzoyl peroxide;

Menthol and other "cooling" agents;

Sodium sulfacetamide and derivatives;

Antifungal agents (such as imidazole derivatives, polyene compounds, allylamine compounds);

Serine protease (kallikrein) inhibitors (such as aminocaproic acid);

Anesthetics (such as lidocaine, tetracaine, prilocaine, benzocaine, bupivacaine, mepivacaine, dibucaine, etidocaine, butacaine, cyclomethycaine, hexylcaine, proparacaine, and ropivacaine).

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

Example 1

Rat Blood Flow Assay

Background

Rosacea can be triggered by heat exposure. The physiological sympathetic nervous system-mediated response to body cooling is cutaneous vasoconstriction and the response to body warming is cutaneous vasodilation. α-adrenergic agonists that act on the sympathetic nervous system outflow can regulate cutaneous blood flow in response to temperature changes.

Method

A laser Doppler microvascular perfusion monitor (laser Doppler flowmetry technique, LDP) was used to monitor red blood cell perfusion in the microvasculature of the hind foot pad. The laser doppler flowmetry (LDP) is an OxyFlo Microvascular Perfusion Monitor, from Oxford Optronix LTd. UK.

Briefly, 15 µL of test articles was applied topically once, or repeatedly (once daily for 4 consecutive days) to one hind foot pad of anaesthetized hairless CD rats and 15 µL of vehicle was applied to the other footpad.

At various timepoints up to 8 hrs following the last test article administration, dynamic blood flow changes were measured and recorded every 15 seconds for 4 minutes per temperature interval for 5 intervals (22° C.→37° C.→4° C.→37° C.→22° C.). Rats were placed on a 37° C. heat pad to increase their temperature and on an ice pad to decrease their temperature to 4° C. The levels of blood flow in the two paws were compared.

FIG. 1 shows topical (S)-(+)-7-(1H-Imidazol-4-ylmethyl)-5,6,7,8-tetrahydro-quinoline significantly inhibits 37° C. induced vessel dilation for up to 4 hrs following single topical dosing to the skin at a concentration of 0.1%. Following 4 days of topical dosing (once per day), the duration of statistically significant inhibition is increased to at least 6 hrs. The % blood flow inhibition is calculated as the % difference in the AUC of peak 1 (first 8 min heating and cooling interval) of the laser doppler recordings between the drug-treated and vehicle-treated paws. Data are the mean % inhibition values from 8-10 rats per group.

This data demonstrates that topical (S)-(+)-7-(1H-Imidazol-4-ylmethyl)-5,6,7,8-tetrahydro-quinoline can inhibit heat-induced cutaneous blood vessel dilation (or overall cutaneous blood flow) in rats, and the effect of one topical application (15 µl of a 0.1% gel) lasts for at least 4 hours. There is an extended duration of at least 6 hrs following 4-day repeat dosing.

Example 2

In Vitro Human Skin Permeability Assay

Human, ex vivo, trunk skin was cut into multiple smaller sections large enough to fit on nominal 2 cm$^2$ static Franz diffusion cells. The dermal receptor compartment was filled to capacity with receptor solution consisting of 0.1× phosphate buffered solution with 0.1% Oleth-20, and the epidermal chamber (chimney) is left open to ambient laboratory environment. The cells were placed in a diffusion apparatus in which the receptor solution in contact with the underside of the dermis was stirred magnetically at ~600 RPM and its temperature maintained to achieve a skin surface temperature of 32.0±1.0° C.

To assure the integrity of each skin section, its permeability to tritiated water was determined before application of the test products. Skin specimens in which absorption of $^3H_2O$ was less than 1.56 µL–equ/cm$^2$ were considered acceptable.

(S)-(+)-7-(1H-Imidazol-4-ylmethyl)-5,6,7,8-tetrahydro-quinoline was applied to three (3) replicate sections of the same donor skin for each donor, evaluating three (3) donors for the designated dose duration. A dose of 5 mg formulation/cm$^2$/skin section was evenly dispersed and rubbed into the skin surface using a glass rod. At designated time points and at the end of the study dose duration, the receptor solution was removed in its entirety, and a predetermined volume aliquot saved for subsequent analysis. After the last receptor sample was collected, the donor compartment (chimney) was removed, and the surface of the skin was cleansed twice to collect any un-absorbed formulation from the skin surface. Following the surface cleanse, the skin was tape stripped to remove the stratum corneum. The tape strips were extracted overnight in acetonitrile and analyzed for content of the compound of interest. The skin was then removed from the diffusion cell, split into epidermis and dermis, and each skin sample extracted overnight in 50%:50% (v/v) ethanol/water or 50%:50% (v/v) methanol water for epidermis and dermis, respectively. The skin section samples were analyzed for content of (S)-(+)-7-(1H-Imidazol-4-ylmethyl)-5,6,7,8-tetrahydro-quinoline. All samples were stored at ~−20° C. (±15° C.) pending analysis. Quantitation of (S)-(+)-7-(1H-Imidazol-4-ylmethyl)-5,6,7,8-tetrahydro-quinoline was analyzed by liquid chromatography with tandem mass spectrometry (PLC/MS).

Replicates within donors were averaged and the standard deviation calculated for each key parameter. Within donor averages were then collated and the across donor population mean with standard error of the mean calculated.

Figure 2:
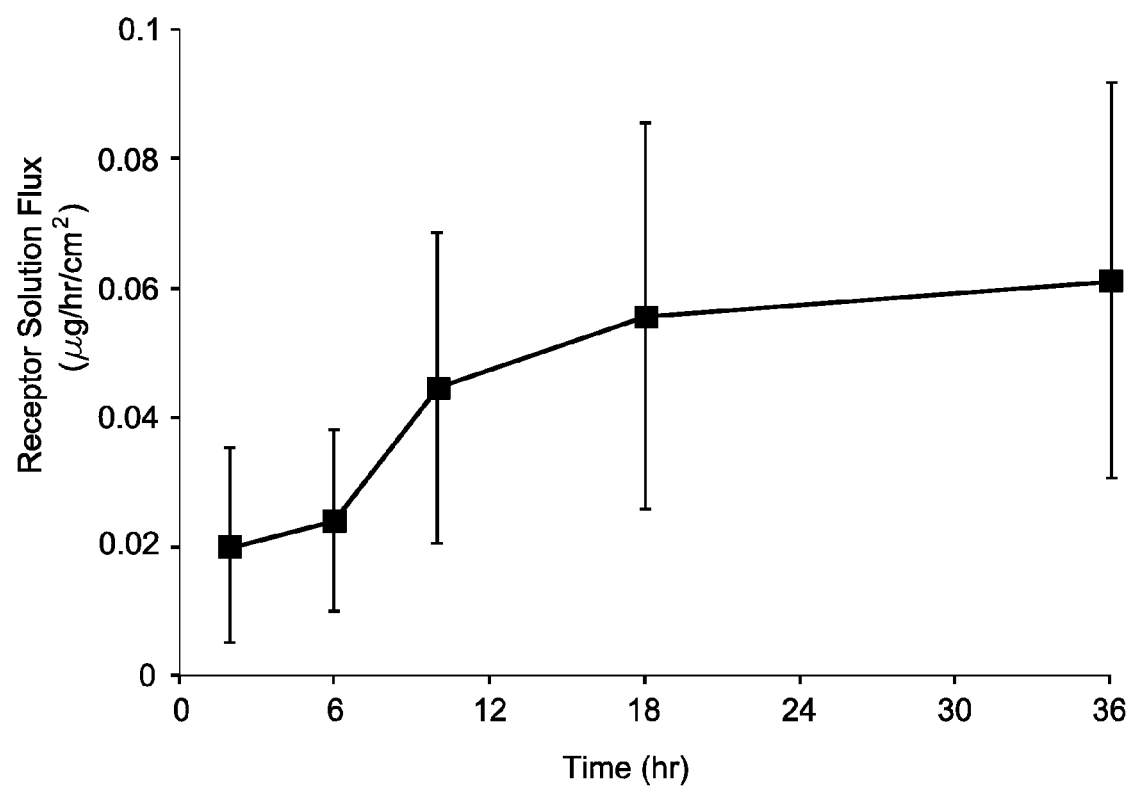
FIG. 2 shows the rate of percutaneous absorption as the flux of (S)-(+)-7-(1H-Imidazol-4-ylmethyl)-5,6,7,8-tetrahydro-quinoline that appears in the receptor solution under the skin in an ex vivo human trunk skin preparation.

FIG. 2 shows the rate of percutaneous absorption as the flux of (S)-(+)-7-(1H-Imidazol-4-ylmethyl)-5,6,7,8-tetrahydro-quinoline that appears in the receptor solution under the skin after a 0.58% (w/w) dose.

Figure 3:
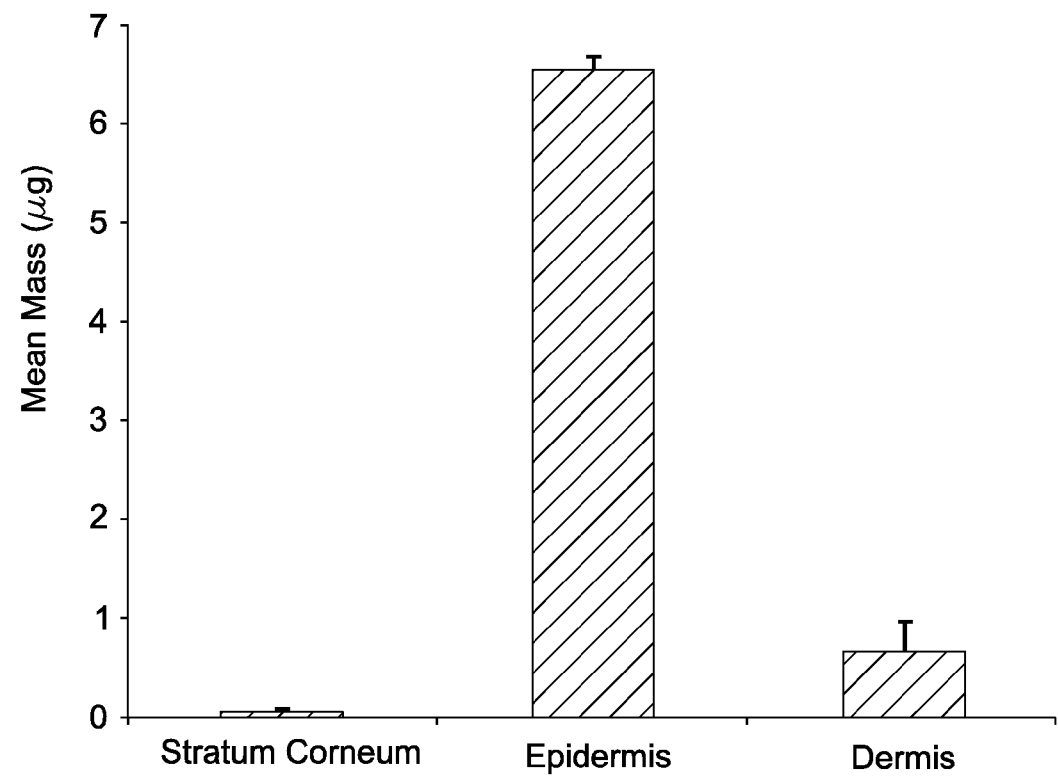
FIG. 3 shows the distribution of (S)-(+)-7-(1H-Imidazol-4-ylmethyl)-5,6,7,8-tetrahydro-quinoline following a 48 hour dose exposure to ex vivo human trunk skin as a mass recovered.
Figure 3:
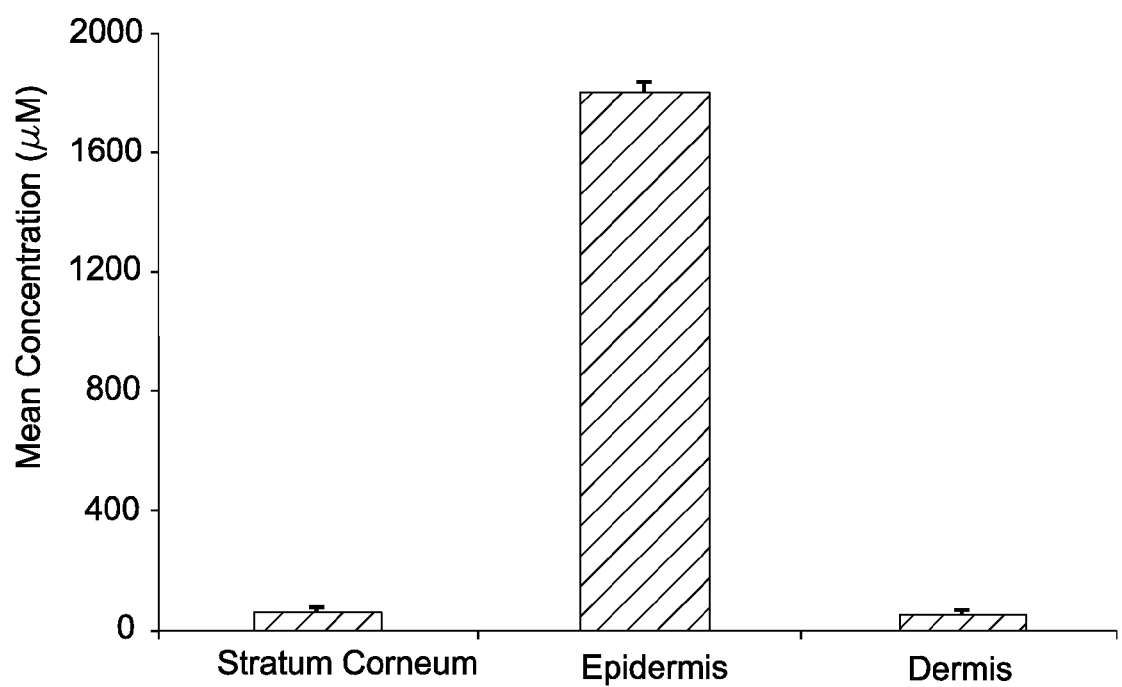

FIG. 3 shows the distribution of (S)-(+)-7-(1H-Imidazol-4-ylmethyl)-5,6,7,8-tetrahydro-quinoline in each skin layer following a 48 hour dose exposure of a 0.58% (w/w) dose to ex vivo human trunk skin as a mass recovered.

The data indicate that (S)-(+)-7-(1H-Imidazol-4-ylmethyl)-5,6,7,8-tetrahydro-quinoline does penetrate into and through ex vivo human trunk skin using the in vitro Franz diffusion cell. The increased rate of flux at the 18 and 36 hr timepoints (FIG. 2) and the higher concentration in the epidermis (FIG. 3) suggests that the drug depots in the skin, which is consistent with a long duration of action and extended duration following repeated dosing.

Example 3

LL-37-Induced Skin Inflammation Mouse Model

Background

Rosacea skin is associated with increased levels of LL-37 cathelicidin compared to normal skin. Intradermal injection of LL-37 into mice induces skin inflammation that is similar to that seen in rosacea skin (Yamasaki 2007).

Method (S)-(+)-7-(1H-Imidazol-4-ylmethyl)-5,6,7,8-tetrahydro-quinoline gel or its corresponding vehicle was applied to the dorsal surface of the ears of BALB/c mice. One hour following application, the left ear was intradermally injected with LL-37 peptide and the right ear was injected with phosphate-buffered saline (PBS). Ear thickness measurements were made with a digital caliper (Mitutoyo) at various timepoints up to 8 hrs post-injection with LL-37. Ear swelling is an indicator of inflammation.

Figure 4:
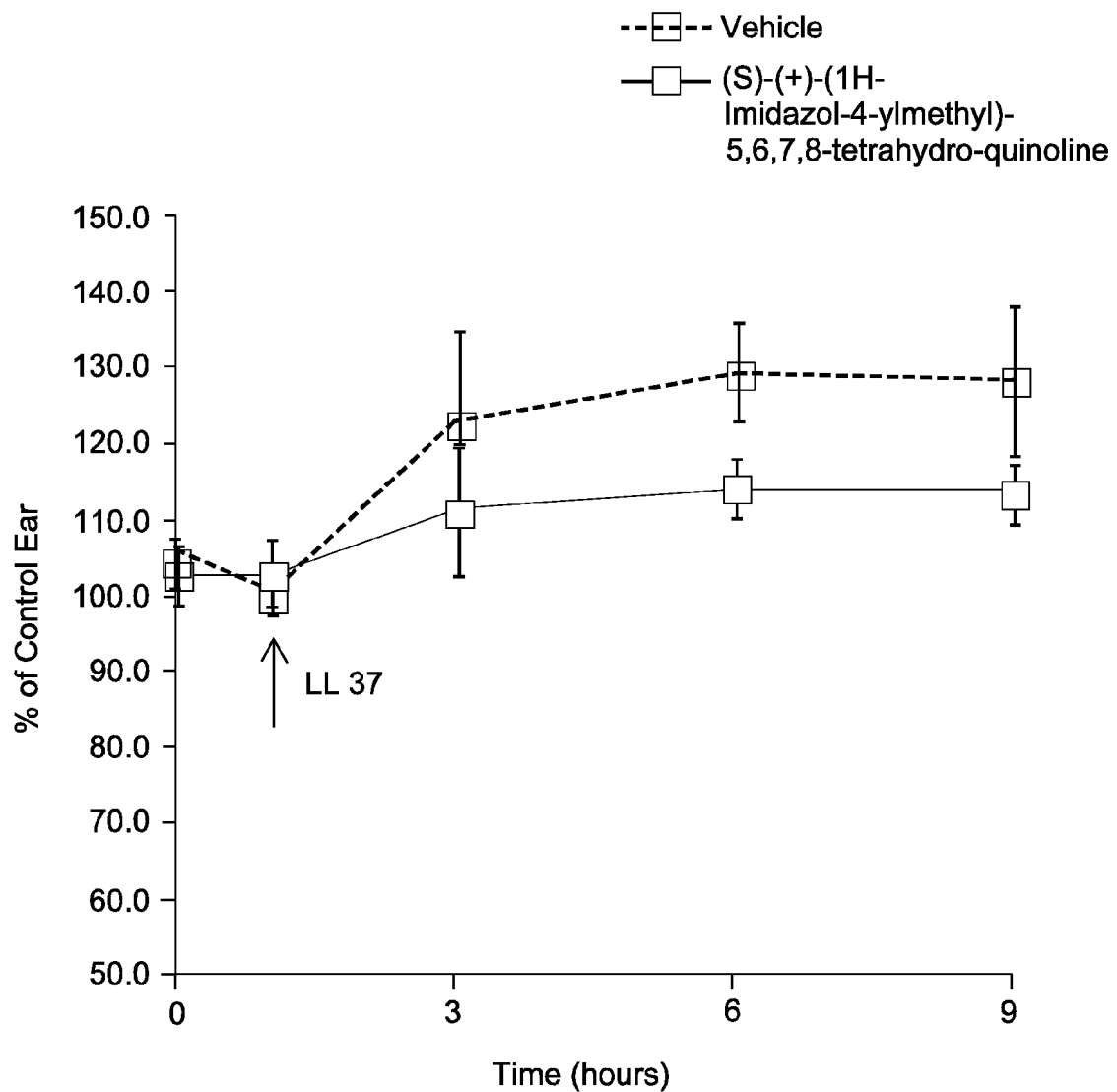
FIG. 4 shows Inhibition of LL-37-induced mouse skin inflammation after topical treatment with (S)-(+)-7-(1H-Imidazol-4-ylmethyl)-5,6,7,8-tetrahydro-quinoline.

FIG. 4 shows statistically significant inhibition of LL-37-induced skin inflammation at 6 and 9 hrs after topical treatment with (S)-(+)-7-(1H-Imidazol-4-ylmethyl)-5,6,7,8-tetrahydro-quinoline. The data are the mean values from 9-10 mice per group.

The data indicates that topical administration of (S)-(+)-7-(1H-Imidazol-4-ylmethyl)-5,6,7,8-tetrahydro-quinoline has an anti-inflammatory effect that is relevant to the treatment of rosacea.

Example 4

Ultraviolet B-Induced Mouse Sunburn Model

Background

Rosacea can be triggered by exposure to ultraviolet (UV) light. Exposure of hairless mice to UVB irradiation results in a sunburn-like response characterized by erythema, cutaneous blood vessel dilation, tactile hypersensitivity and inflammation that persists for at least 48 hrs.

Method

SKH1 hairless mice, lying on their stomachs with their left sides covered, were exposed to UVB at an intensity of 120 mJ/cm$^2$ for 91 sec. Approximately 30 min after irradiation, (S)-(+)-7-(1H-Imidazol-4-ylmethyl)-5,6,7,8-tetrahydro-quinoline gel or its corresponding vehicle was applied topically to a region of the back and the dorsal surface of the ears. At various timepoints up to 48 hrs post UVB-irradiation, the following assessments were made:

1. Vasculature area in the exposed and unexposed ears by image analysis of digital photos using ImagePro Premier (Media Cybernetics) software. Images are converted to grayscale, expanded and thresholding, based on each ear's baseline pixel values, is applied to the images. Thresholding differentiates the desired "object" features (i.e. vasculature network) from the background (i.e. skin tissue). The "object" pixels are then quantified and reported as the vasculature area.

2. Erythema on the exposed and unexposed back using a Chromameter (Konica Minolta).

3. Tactile hypersensitivity assessment using a paint brush test. The hypersensitivity is assessed by light stroking of the flank of the mice with a small paint brush every 5 min over 35 min. The behavioral response is scored as follows: 0, no response; 1, mild squeaking with attempts to move away from the brush; 2, vigorous squeaking evoked by the brush, biting at the brush and strong efforts to escape. The scores at the eight time points are summed so the maximum hypersensitivity score for each mouse can be 16. The exposed (right) and unexposed (left) flanks were scored independently.

Figure 5:
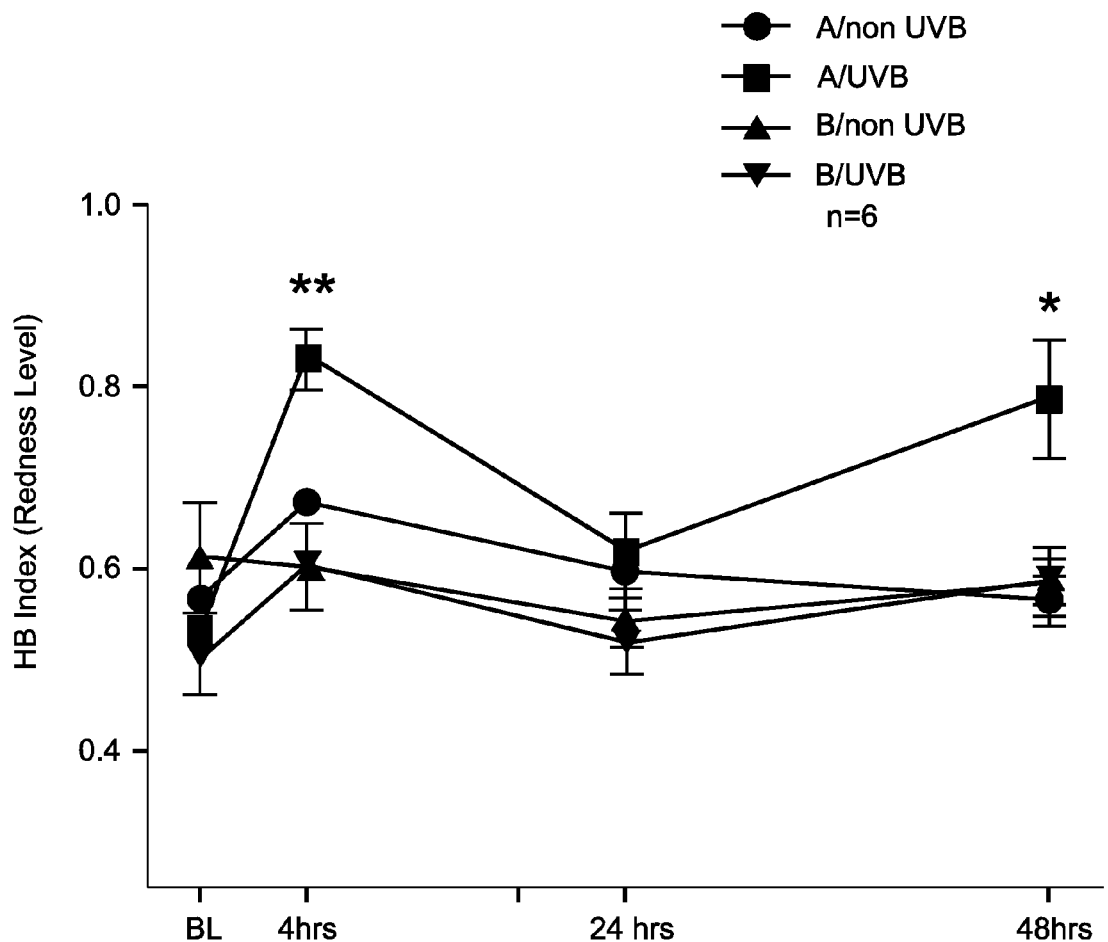
FIG. 5 shows reduction of UVB-induced mouse skin erythema (redness) for at least 48 hrs following treatment with (S)-(+)-7-(1H-Imidazol-4-ylmethyl)-5,6,7,8-tetrahydro-quinoline.

FIG. 5 shows that topical dosing of (S)-(+)-7-(1H-Imidazol-4-ylmethyl)-5,6,7,8-tetrahydro-quinoline to the back 30 min following UVB exposure results in a statistically significant reduction of erythema (measured with a chromameter) to nearly baseline levels that lasts for at least 48 hrs. Data are the mean of values from 6 mice per group.

Figure 6:
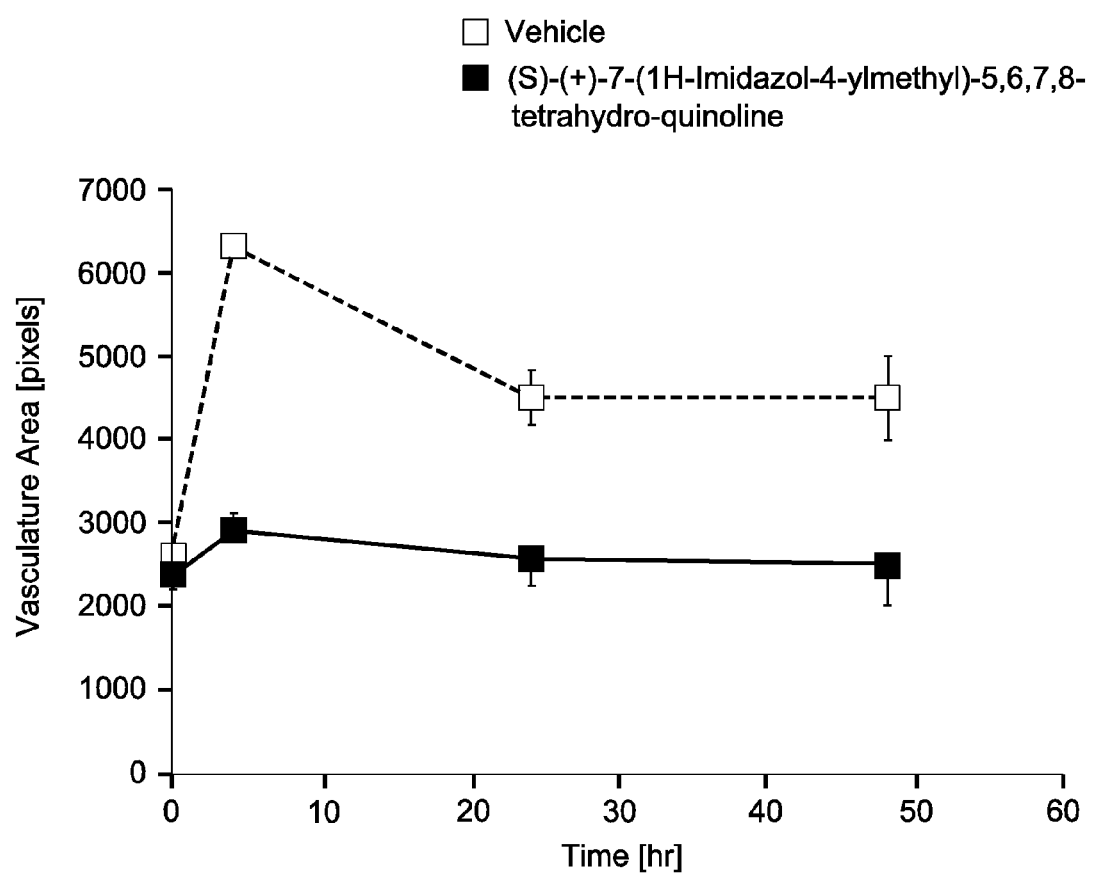
FIG. 6 shows reduction of UVB-induced cutaneous vessel dilation in mouse ears for at least 48 hrs following treatment with (S)-(+)-7-(1H-Imidazol-4-ylmethyl)-5,6,7,8-tetrahydro-quinoline.

FIG. 6 shows that topical dosing of (S)-(+)-7-(1H-Imidazol-4-ylmethyl)-5,6,7,8-tetrahydro-quinoline to the ear 30 min following UVB exposure results in statistically significant cutaneous vasoconstriction (measured as a reduction of cutaneous vasculature area) to nearly baseline levels that lasts for at least 48 hrs. Data are the mean of values from 6 mice per group.

Figure 7:
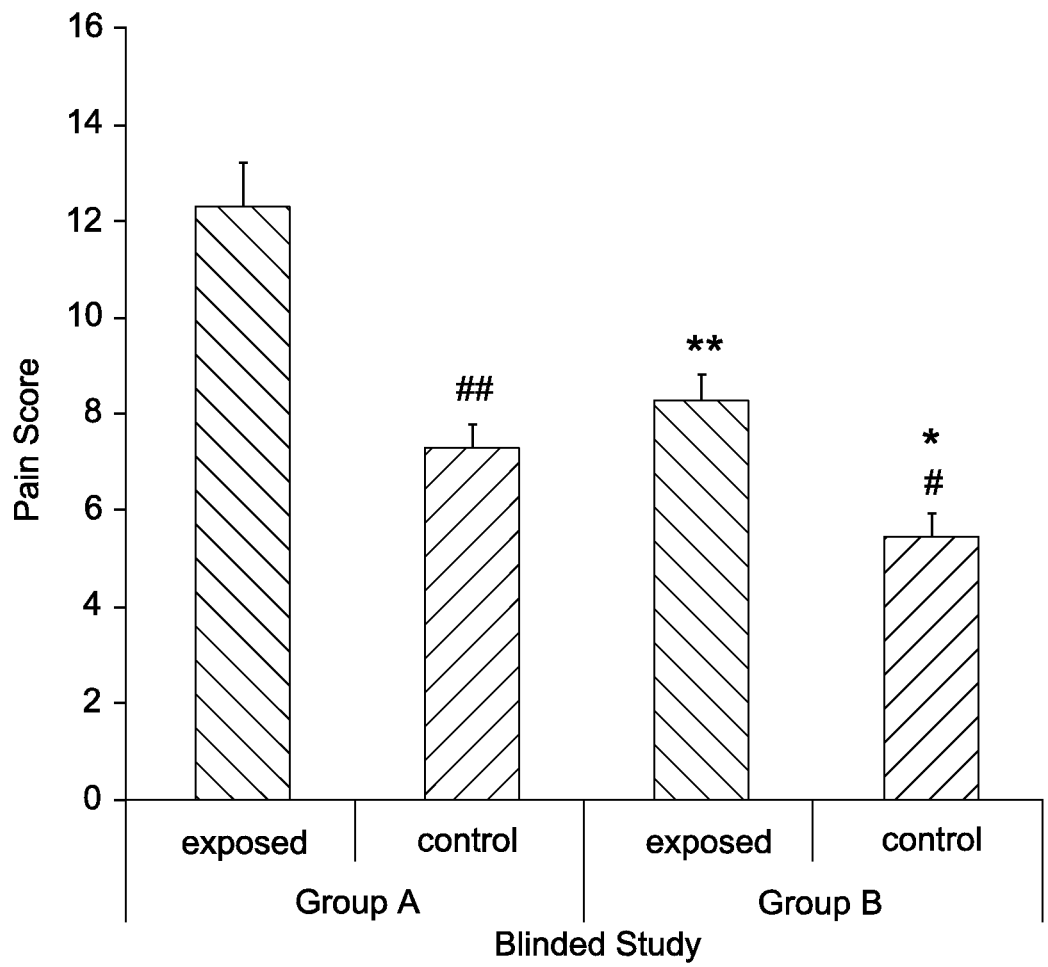
FIG. 7 shows reduction of tactile hypersensitivity in UVB exposed mouse skin 4 hrs following treatment with (S)-(+)-7-(1H-Imidazol-4-ylmethyl)-5,6,7,8-tetrahydro-quinoline.

FIG. 7 shows that topical dosing of (S)-(+)-7-(1H-Imidazol-4-ylmethyl)-5,6,7,8-tetrahydro-quinoline to the back 30 min following UVB exposure results in a statistically significant reduction of tactile hypersensitivity (scored by the response to stroking with a paint brush) assessed 4 hrs following UVB irradiation. There was a reduction in hypersensitivity on both the UV-exposed and control sides. Data are the mean of values from 6 mice per group.

The data indicate that topical administration of (S)-(+)-7-(1H-Imidazol-4-ylmethyl)-5,6,7,8-tetrahydro-quinoline has a long-lasting beneficial effect on inflammation, erythema (redness) and hypersensitivity, which are signs and symptoms of many skin diseases and conditions. The findings have particular relevance to the treatment of sunburn, rosacea and psoriasis.

Example 5

Mouse Model of UV-Induced Erythema

The right backs of male SKH1 hairless mice were exposed to 120 mJ/cm$^2$ UVB radiation, while the left sides were shielded. At either 20 minutes, 4 hours, or 8 hours following UVB exposure, a single dose of 0.1% (S)-(+)-7-(1H-Imidazol-4-ylmethyl)-5,6,7,8-tetrahydro-quinoline was applied topically to their backs. An additional group with vehicle applied topically at 20 minutes post UVB exposure served as a control. Samples of skin from the backs from both left and right sides were collected 48 hours following UVB exposure and examined histologically.

Damage to the dermis and epidermis was observed in UV-exposed skin and was most apparent histologically at 48 hours after exposure.

Application of 0.1% (S)-(+)-7-(1H-Imidazol-4-ylmethyl)-5,6,7,8-tetrahydro-quinoline 20 minutes following UVB exposure to the back skin significantly improved the outcome of healing, with a shift toward adaptive epidermal hyperplasia and a reduction of epidermal necrosis, and separation from underlying dermis. Additionally, edema, mixed inflammatory cell infiltrates and vascular congestion of the underlying dermis was also significantly reduced, indicating that 0.1% (S)-(+)-7-(1H-Imidazol-4-ylmethyl)-5,6,7,8-tetrahydro-quinoline has anti-inflammatory as well as vasoconstrictive effects. The overall effectiveness of this adaptive response was greatly improved by treatment with 0.1% (S)-(+)-7-(1H-Imidazol-4-ylmethyl)-5,6,7,8-tetrahydro-quinoline at either 20 minutes, 4 hours, or 8 hours post-UVB exposure in the majority of mice. (Table 1). The overall healing was good to excellent in 75% of mice treated at 20 minutes, 50% of mice treated at 4 hours, and 60% of mice treated at 8 hours post UVB exposure, as compared to 13% of vehicle treated mice. In contrast epidermal failure (moderate to marked separation and necrosis and thus loss of the epidermal barrier function) was present in 50% of the vehicle treated mice, but only seen in one (8%) of the mice treated with 0.1% (S)-(+)-7-(1H-Imidazol-4-ylmethyl)-5,6,7,8-tetrahydro-quinoline up to 8 hours following UVB exposure.

Therefore this study shows that even with delayed treatment up to 8 hours following UVB exposure, 0.1% (S)-(+)-7-(1H-Imidazol-4-ylmethyl)-5,6,7,8-tetrahydro-quinoline topical treatment improves the healing potential of UVB-exposed skin in the majority of SKH1 Hairless mice.

Table 1 shows that topical dosing of 0.1% (S)-(+)-7-(1H-Imidazol-4-ylmethyl)-5,6,7,8-tetrahydro-quinoline to the back at 20 min, 4 hr, or 8 hrs following 120 mJ/cm$^2$ of UVB exposure results in an overall improvement in inflammation compared to the vehicle control as assessed by histopathological endpoints: epidermal hyperplasia, disorganization, separation, and necrosis; dermal edema, inflammatory infiltrates, and vascular congestion. Each endpoint is graded on a scale of 0-4 (0=no findings, 1=minimal, 2=mild, 3=moderate, 4=marked). Data are expressed as the mean of values from 6 mice per group.

TABLE 1

| | EPIDERMIS | | | | DERMIS | | |
| --- | --- | --- | --- | --- | --- | --- | --- |
| | Hyperplasia | Disorganization | Separation | Necrosis | Edema | Infiltrates | Congestion |
| Vehicle | 1.8 | 3.5 | 2.0 | 2.8 | 2.4 | 2.5 | 2.6 |
| 20 min | 3.0 | 2.0 | 0.3 | 0.5 | 0.5 | 0.8 | 1.0 |
| 4 hr | 2.3 | 3.0 | 1.3 | 1.3 | 2.0 | 2.0 | 1.8 |
| 8 hr | 3.3 | 2.0 | 1.3 | 1.0 | 1.5 | 0.8 | 1.0 |

What is claimed is:

1. A method for treating a skin condition selected from the group consisting of sunburn, erythema of the skin, and cutaneous hyperactivity with dilation of blood vessels of the skin, the method comprising administering to a patient in need thereof a pharmaceutical composition comprising a therapeutically effective amount of (S)-(+)-7-(1H-imidazol-4-ylmethyl)-5,6,7,8-tetrahydroquinoline, or an individual tautomer thereof, or a pharmaceutically acceptable salt of any of the foregoing.

2. The method according to claim 1, wherein the condition is sunburn.

3. The method according to claim 1, wherein the condition is erythema of the skin.

4. The method according to claim 1, wherein the condition is cutaneous hyperactivity with dilation of blood vessels of the skin.

* * * * *

UNITED STATES PATENT AND TRADEMARK OFFICE
CERTIFICATE OF CORRECTION

PATENT NO. : 9,283,217 B2
APPLICATION NO. : 13/830311
DATED : March 15, 2016
INVENTOR(S) : Mohammed I. Dibas et al.

It is certified that error appears in the above-identified patent and that said Letters Patent is hereby corrected as shown below:

Title page, item (54), in column 1, in "Title", lines 2-3, delete "7-(1 H-IMIDAZOL" and insert -- 7-(1H-IMIDAZOL --, therefor.

Specification

In column 10, line 62, delete "A);" and insert -- A, ketoprofen, indomethacin, naproxen); --, therefor.

In column 11, line 5, delete "propanolol," and insert -- propranolol, --, therefor.

In column 11, line 43, delete "LDP)" and insert -- LDF) --, therefor.

In column 11, line 45, delete "(LDP)" and insert -- (LDF) --, therefor.

In column 11, line 47, delete "LTd." and insert -- Ltd. --, therefor.

In column 12, line 37, delete "time points" and insert -- timepoints --, therefor.

In column 14, line 10, delete "time points" and insert -- timepoints --, therefor.

Claims

In column 16, line 22, in Claim 1, delete "8-tetrahydroquinoline," and insert -- 8-tetrahydro-quinoline, --, therefor.

Signed and Sealed this
Nineteenth Day of July, 2016

Michelle K. Lee
*Director of the United States Patent and Trademark Office*